(12) United States Patent
Light et al.

(10) Patent No.: US 6,766,693 B1
(45) Date of Patent: Jul. 27, 2004

(54) AVERAGED GUIDED WAVE INSPECTION TECHNOLOGY FOR RIBBON CABLE

(75) Inventors: Glenn M. Light, San Antonio, TX (US); Ali Minachi, San Antonio, TX (US); Kevin M. Carpenter, Frisco, TX (US)

(73) Assignee: Southwest Research Institute, San Antonio, TX (US)

( * ) Notice: Subject to any disclaimer, the term of this patent is extended or adjusted under 35 U.S.C. 154(b) by 2 days.

(21) Appl. No.: 10/454,349

(22) Filed: Jun. 4, 2003

(51) Int. Cl.[7] .................................................. G01N 9/24
(52) U.S. Cl. ............................ 73/622; 73/624; 73/634
(58) Field of Search ......................... 73/622, 624, 626, 73/627, 628, 634

(56) References Cited

U.S. PATENT DOCUMENTS

| | | | |
|---|---|---|---|
| 3,929,006 A | * 12/1975 | Boggs et al. | .................. 73/609 |
| 4,193,306 A | 3/1980 | Flaherty et al. | |
| 4,658,649 A | 4/1987 | Brook | |
| 5,156,636 A | * 10/1992 | Kuljis | .......................... 73/597 |
| 5,158,086 A | * 10/1992 | Brown et al. | ................ 600/459 |
| 5,386,395 A | 1/1995 | Le Guerinel et al. | |
| 5,413,107 A | * 5/1995 | Oakley et al. | .............. 600/463 |
| 5,457,994 A | * 10/1995 | Kwun et al. | ................... 73/587 |
| 5,665,907 A | 9/1997 | Sheen et al. | |
| 5,767,410 A | 6/1998 | Lareau et al. | |
| 5,932,806 A | 8/1999 | Rose et al. | |
| 6,148,672 A | * 11/2000 | Cawley et al. | ................ 73/622 |

OTHER PUBLICATIONS

Rose, Joseph L and Zhao, Xiaoliang; Pipe Elbow Inspection with Guided Waves.

* cited by examiner

Primary Examiner—Hezron Williams
Assistant Examiner—Jacques M. Saint-Surin
(74) Attorney, Agent, or Firm—Gunn & Lee, PC

(57) ABSTRACT

Averaged guided wave inspection method for a throttle cable is disclosed. Access to the engine end of the throttle cable is obtained and a transducer is applied to an end of the ribbon cable. The transducer generates an ultrasonic guided wave in the cable. The ultrasonic guided wave propagates down the entire length of the cable and reflects back from any discontinuity in the cross section of the ribbon cable. By determining the time needed for the reflected wave to travel back to the receiver, the location of any defect along the length of the cable can be determined. By moving the ribbon cable and transducer to different positions with respect to the sheath of the throttle cable, repeating the prior steps and averaging, unwanted noise caused by external influences is eliminated.

21 Claims, 6 Drawing Sheets

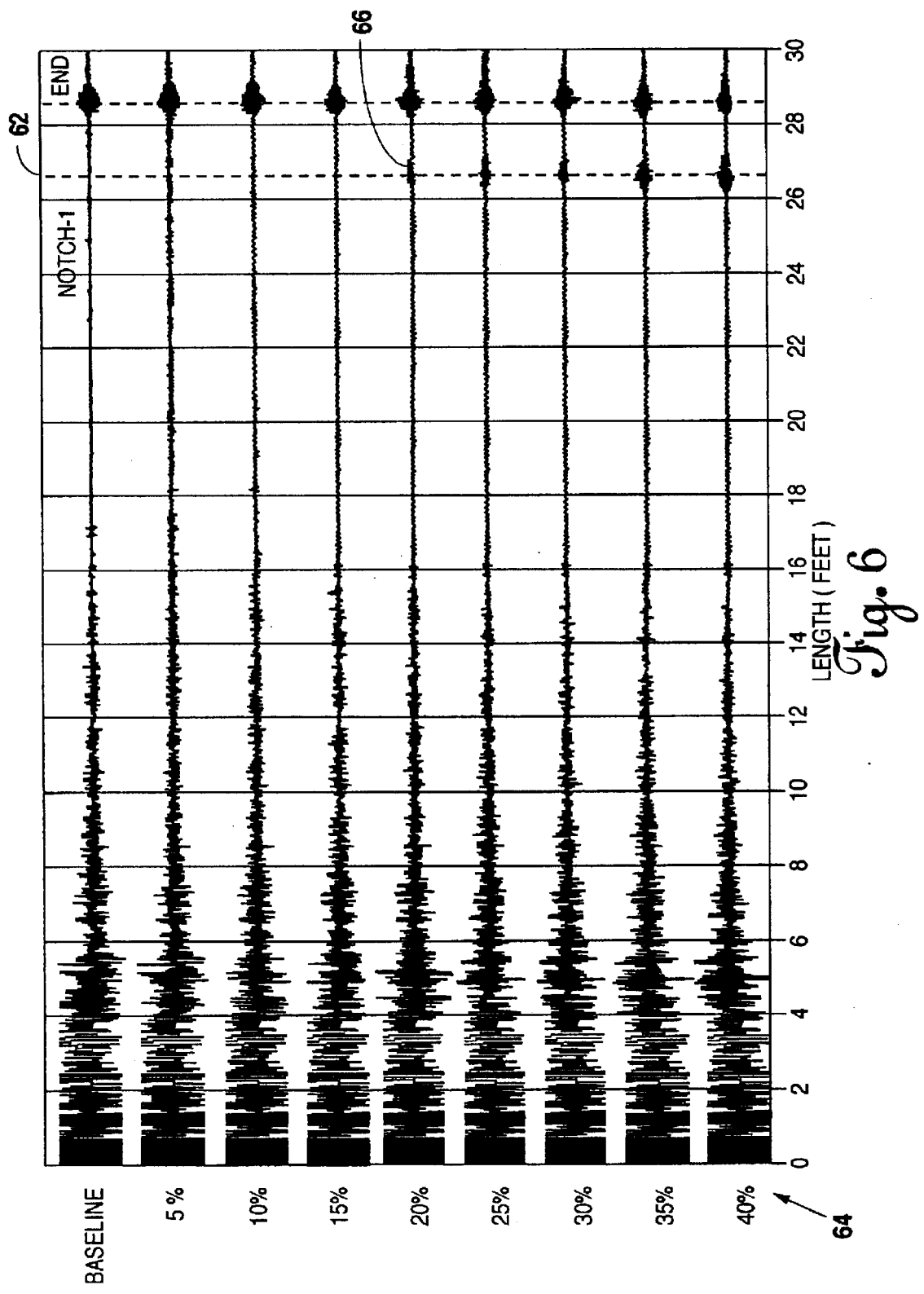

AVERAGED GUIDED WAVE INSPECTION TECHNOLOGY FOR RIBBON CABLE

This invention was made in part with government support under Contract No. F04606-98-D-0002 awarded by the United States Air Force. The United States Government has certain rights in this invention.

BACKGROUND OF THE INVENTION

1. Field of the Invention

Applicant's invention relates to an averaged guided wave inspection technology for ribbon cable.

2. Background Information

There are throttle cables in many aircraft, particularly the AO/A-10 Thunderbolt, that have the potential for failure during routine flying activities. The failure of the throttle cable can result in loss of throttle control and can lead to critical failure or loss of the aircraft. The throttle cable consists of a steel ribbon cable approximately 0.05 inch by 0.200 inch in cross-sectional dimension and ranging from approximately 26 to 32 feet in length that is contained in a stainless steel sheath casing and supported by a large number of stationary ball bearings inside the sheath. This ribbon cable directly connects the engine throttle to the throttle control in the cockpit. The stationary ball bearings allow the ribbon inside the throttle cable to move freely through the sheath. The throttle cable is strung between the cockpit and engines through the fuselage and in the process must go through several bends. An analysis of the failure modes seems to indicate that cycling the ribbon cable through these bends can lead to fatigue cracking and ultimately to failure of the ribbon. At the present time, during normal maintenance, these cables are given a force test to ensure that the ribbon cable moves freely inside the sheath. However, if the cable passes the force test there is no assurance that the ribbon does not have a defect or that the whole cable is not defective. Presently, there is no way to inspect the ribbon without the costly process of removing the entire throttle cable from the aircraft. Therefore, there is a need to develop a nondestructive evaluation technique that would allow inspection of these cables to detect any abnormalities or defects in the ribbon before failure. Since the ribbon cable is completely inaccessible to any probe except for a few inches at the end of the cable where it attaches the engine, the inspection technique must inspect the entire ribbon length from the accessible end.

The present invention accomplishes this goal and provides a nondestructive technique to inspect the throttle cables of aircraft, particularly A-10 aircraft. This inspection technique inspects the ribbon cable from its accessible end and provides complete inspection of the entire length of the ribbon by utilizing an averaged guided wave technology. In addition, this technology has application for inspection of cable in other items as well.

An ultrasonic guided wave approach was chosen that would allow an ultrasonic transducer to be placed on the accessible end of the ribbon cable and generate a guided wave that would travel down the entire length of the ribbon. This guided wave was capable of detecting small defects that would show up in the plot of reflected signal strength as a function of time (called an A-scan). However, the initial evaluation of the guided wave approach showed that the contact points between the ball bearings at the bend regions and throughout the length of the throttle cable caused reflections of guided waves as well. Since the ball bearings were spaced approximately every ⅝ inch down the length of the cable, a large number of reflected signals in the A-scan are due to the contact between ball bearings at the bend regions and the ribbon cable were observed. This caused false defect calls in addition to the masking of real defects in the bend regions. Unfortunately, the false calls were not random and simple averaging of the A-scans did not eliminate them.

However, it was found that one way to reduce the effect of these signals was to average the guided wave data collected while the ribbon was being moved back and forth through the cable sheath. This would mean that the temporal location of the reflection of the ball bearing contact with the ribbon in one waveform would be different than in the following waveforms because the ball bearings were fixed in the sheath and, as the ribbon moved inside the sheath, its relative position with respect to the ball bearings would be continually changing. In addition, the relative position of any defect in the ribbon cable stays fixed between the guided wave transducer and the defect. In these circumstances, if guided wave A-scan data is collected and averaged as the ribbon cable is being moved back and forth inside the cable sheath, then signals from the defect will continue to remain constant throughout the averaging process, but signals from the random electronic noise and signals from the ball bearing contact will be diminished because those signals are always changing in time with respect to the transducer's position.

SUMMARY OF THE INVENTION

Applicant's primary object for the present invention is to provide a method of inspecting throttle cables.

It is a further object of the present invention that the inspection system of the present invention gain access to the end of the throttle cable at the engine end and apply a piezoelectric transducer to the ribbon cable to generate an ultrasonic guided wave in the cable.

An additional object of the present invention is when the transducer is attached and coupled to the end of the ribbon cable, it will produce a low frequency guided wave that will propagate down the entire length of the ribbon and reflect back from any discontinuity in the cross section of the ribbon cable.

A further object of the present invention is to provide an averaging technique that allows defects to be distinguishable from other discontinuities.

Yet another object of the present invention is that in this technique, the ribbon cable with the transducer fixed on one end of it is moved to a number of positions in the cable sheath and upon generation, propagation, reflection, and reception of the wave, a waveform of the received reflections versus time is recorded to create a primary A-scan data set.

An additional object of the present invention is that the waveform received from the previous objective is recorded as the ribbon is moved inside the sheath cable.

Still another object of the present invention is for the primary and secondary A-scan data sets to then be averaged to obtain information on the position of any defects in the cable ribbon as distinguished from the ball bearing contact points.

BRIEF DESCRIPTION OF THE DRAWINGS

FIG. 6 is graph of the detection of notch #1 in test cable #3 (Cable laid straight with no clamps) as the notch size is increased from 5% to 50% of cable cross section.

DETAILED DESCRIPTION OF THE PREFERRED EMBODIMENT

The inspection system of the present invention gains access to the end of the throttle cable at the engine end and applies a piezoelectric transducer to the ribbon cable to generate an ultrasonic guided wave in the ribbon. When the transducer is attached and coupled to the end of the ribbon cable, it will produce a low frequency elastic wave that will propagate down the entire length of the ribbon and reflect back from any discontinuity in the cross section of the ribbon cable. By determining the time needed for the reflected wave to travel back to the receiver, the location of the defect along the length of the throttle cable can be determined.

The present inspection system is based mainly on the principle of guided waves. Guided waves are dispersive waves (velocity is a function of frequency) generated when the dimension of the solid body is of the same order or smaller than the acoustic wavelength. Guided waves have energy flow mainly along the direction of the guiding configuration. Such guided waves can be considered elastic perturbations propagating in a solid layer with free boundaries. On the other hand, bulk waves travel along the propagation direction, regardless of the geometry of the propagating medium. Displacements of guided waves are both in the direction of wave propagation and perpendicular to the direction of propagation.

Figure 1:
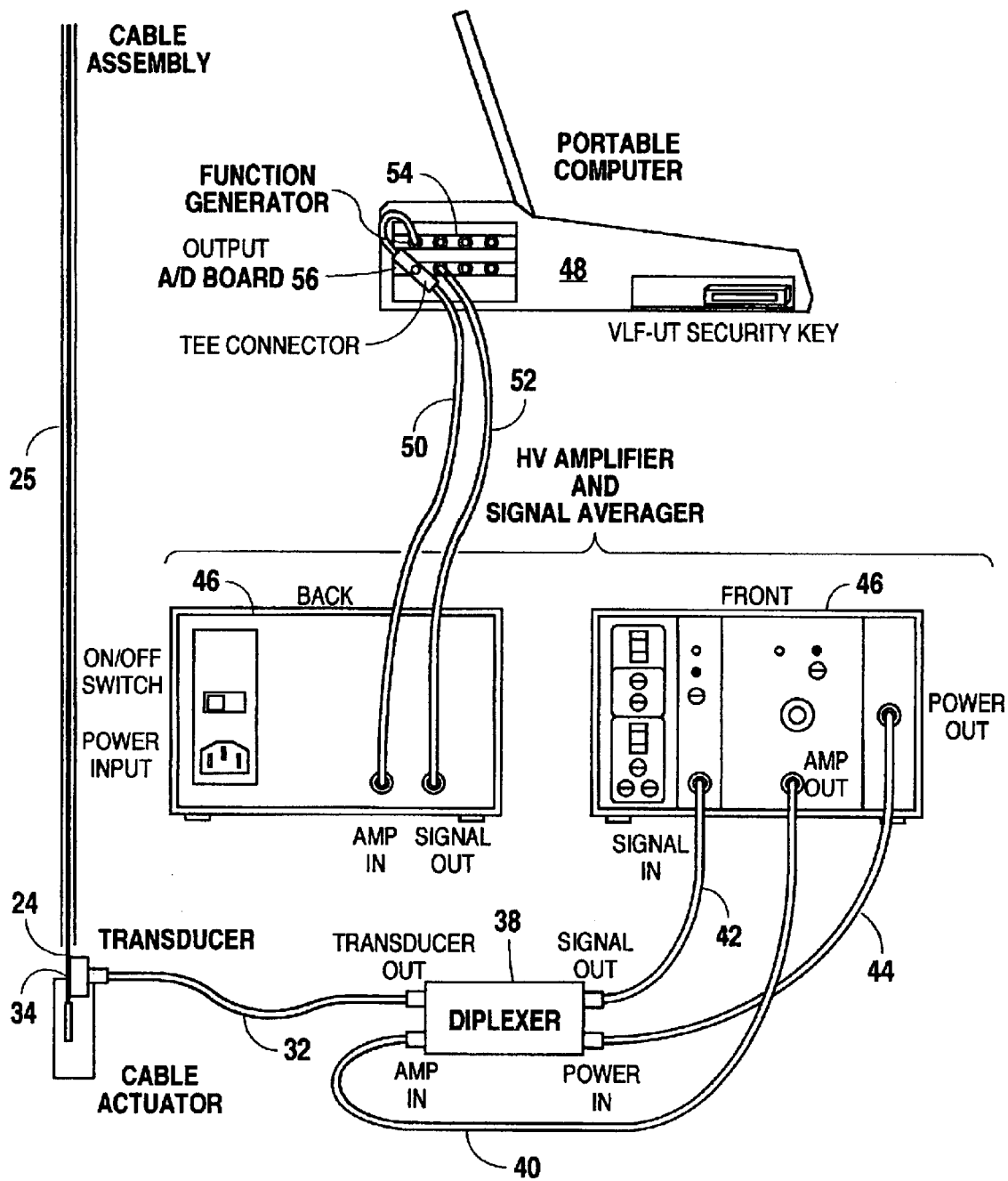
FIG. 1 is a schematic view of the throttle cable inspection system components.

Referring to FIG. 1, the throttle cable inspection system components are shown. Ultrasonic guided waves are introduced into the ribbon cable 24 by a 0.5 inch, 500 kHz transducer 34 with a band width of approximately 200 to 800 kHz that is driven by a very low frequency-ultrasonic test system (VLF-UT). This system consists of software running on a portable computer 48 and hardware to generate the tone burst. An industry-standard architecture (ISA) function generator card 54 situated within the portable computer 48 generates the tone burst, more particularly a gaussian signal, of the required frequency. The tone burst is transmitted to the analog-to-digital (A/D) board 56 where it is digitized. A modified tone burst is transmitted over cable 50. Cable 50 connects the portable computer 48 to a high voltage amplifier 46 at AMP IN. The high voltage amplifier 46 is used to amplify the generated signal of the ISA function generator card 54.

The amplified signal then proceeds out of the high voltage amplifier 46 through AMP OUT and into cable 40. Cable 40 terminates in AMP IN of a diplexer 38. Diplexer 38 separates the transmitting signal from the received signal. Power is provided to diplexer 38 from amplifier 46 through power cable 44. The amplified signal then proceeds from the diplexer 38, out TRANSDUCER OUT, and into coaxial cable 32. Coaxial cable 32 connects to transducer 34. When transducer 34 is attached to ribbon cable 24, the amplified tone burst signal generates ultrasonic vibration at the active face of the transducer 34 where it has attached to the ribbon cable 24. The vibration of transducer 34 is transmitted to the ribbon cable 24, proceeds through the length of throttle cable 25, and is then reflected from any discontinuity in the ribbon and the end of the ribbon. The reflected ultrasonic vibration is returned to transducer 34, and is changed to electrical signal and this signal travels back into coaxial cable 32 and into TRANSDUCER OUT of diplexer 38. The reflected signal then passes out SIGNAL OUT into cable 42 and into SIGNAL IN of amplifier 46. The amplifier 46 amplifies the reflected signal. This amplified, reflected signal then passes through SIGNAL OUT of amplifier 46 into cable 52 and into the A/D board 56 of the portable computer 48. The A/D board 56 in the portable computer 48 captures the amplified, reflected signals from the transducer 34. Finally; the amplified, received signal from the transducer 34 is displayed on the screen of the portable computer 48 and stored in memory of the portable computer 48. When the signal is received, the function generator 54 generates another signal in accordance with programmed instructions and the process is repeated.

Figure 2:
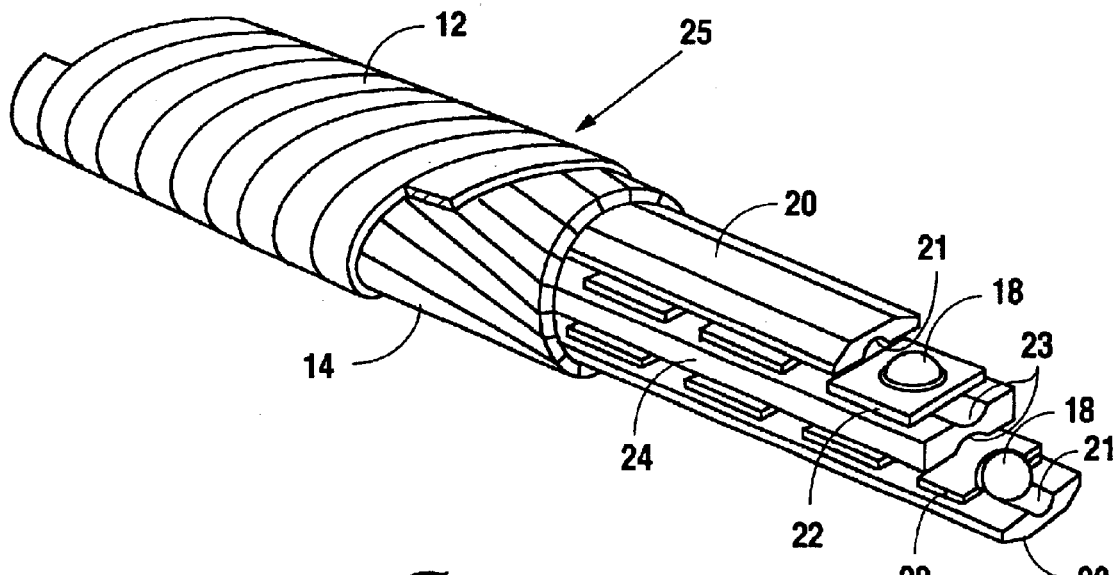
FIG. 2 is a cut away perspective view of throttle cable.
Figure 3:
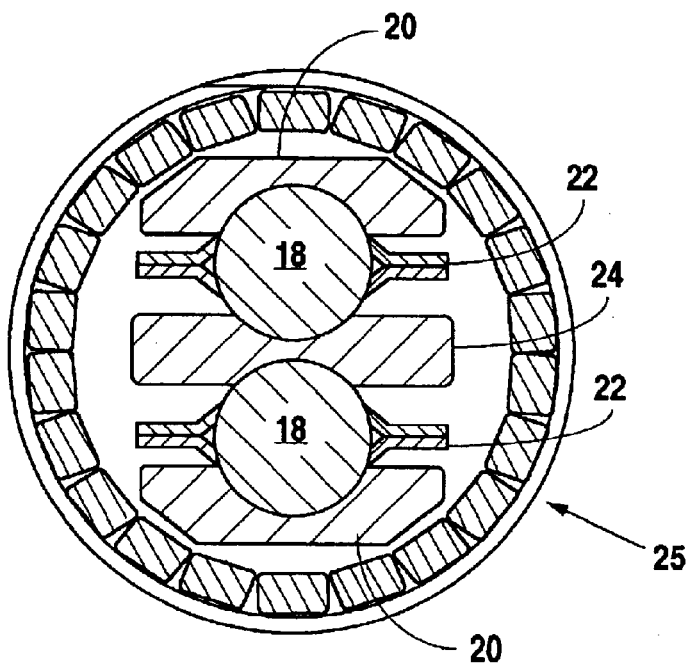
FIG. 3 is an internal cross section of the throttle cable.

Throttle cable 25 is shown in more detail in the internal cross section in FIG. 3 and the cut away perspective in FIG. 2. The throttle cable 25 directly connects the engines in the rear of the aircraft to the throttle control levers in the cockpit at the front of the aircraft. The throttle cable 25 is approximately 26 to 32 feet long. The ribbon cable 24 is approximately 0.05 inches by 0.200 inches in cross section dimension and is normally made from stainless steel. A protective sheath casing 14 encircles the ribbon cable 24. A protective sleeve 12 covers the sheath casing 14. The ribbon cable 24 is supported by a large number of stationary ball bearings 18 on the inside of the sheath casing 14 that hold the ribbon cable 24 and enable the ribbon cable 24 to move freely through the sheath casing 12.

The stationary ball bearings 18 are located between spacer grooves 21 and ribbon grooves 23 and may move along the grooves 21 and 23. Ball bearings 18 are responsible for many of the false signals that can be obtained in the non-averaged guided wave signal. Outer 20 and inner 22 spacers space the ball bearings 18 apart. cut-away view of the throttle cable 25 is shown in FIG. 2. The cable 25 is shown with a protective sleeve 12 and sheath casing 14. Housed within sheath casing 14 are outer spacers 20 and inner spacers 22 which hold ball bearings 18 in place. Located centrally is ribbon cable 24 which is held in its center locations by ball bearings 18.

Figure 4A:
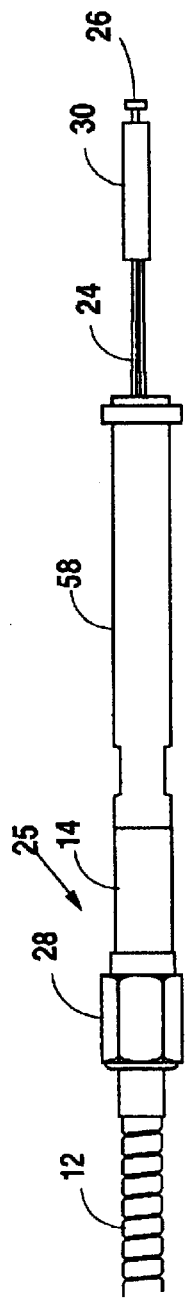
FIG. 4a is a close up view of the engine end of throttle cable incorporating a long sleeve.
Figure 4B:
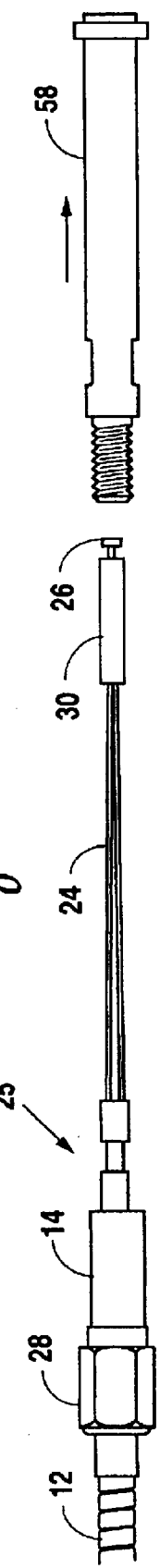
FIG. 4b is a close up view of the engine end of throttle cable with long sleeve removed.
Figure 4C:
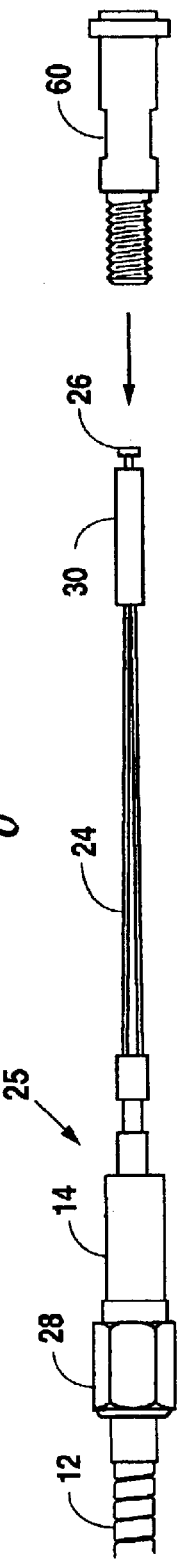
FIG. 4c is a close up view of the engine end of throttle cable with the short sleeve being added.
Figure 4D:
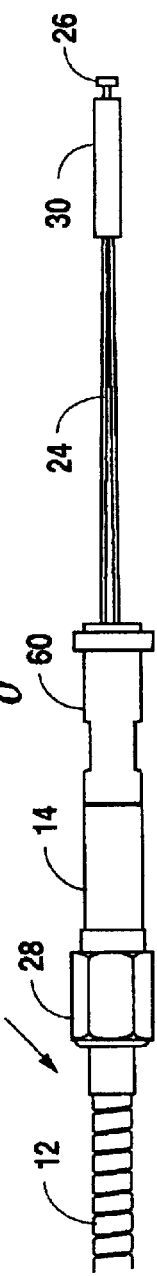
FIG. 4d is a close up view of the engine end of throttle cable incorporating a short sleeve.

In order to inspect the ribbon cable 24 for defects, the transducer 34 must be attached to the engine end of the ribbon cable 24, which has only about one inch of exposed ribbon cable 24. To increase the exposed part of the ribbon cable 24, a long sleeve telescopic spacer 58 at the end of the throttle cable 25 is removed. The telescopic spacer 58 retains the ball bearings 18 in position. FIGS. 4a and 4b are close up views of the engine end of throttle cable 25 with a long sleeve telescopic spacer 58 both attached and detached, respectively. The long sleeve telescopic spacer 58 was replaced with a short sleeve telescopic spacer 60 which is illustrated in more detail in FIGS. 4c and 4d. This shorter sleeve can still hold the ball bearings 18 in position, but also gives a larger exposed space on the ribbon cable 24. The remaining portions of the engine end of throttle cable 25 include knob 26 which hooks into the aircraft engine (not shown). Adjacent knob 26 is enlarged part 30 which attaches to the engine control. Ribbon cable 24 is formed with knob 26 and enlarged part 30, but begins after enlarged part 30. Nut 28 attaches sheath casing 14 to protective sleeve 12 at the end of cable 25.

Figure 5:
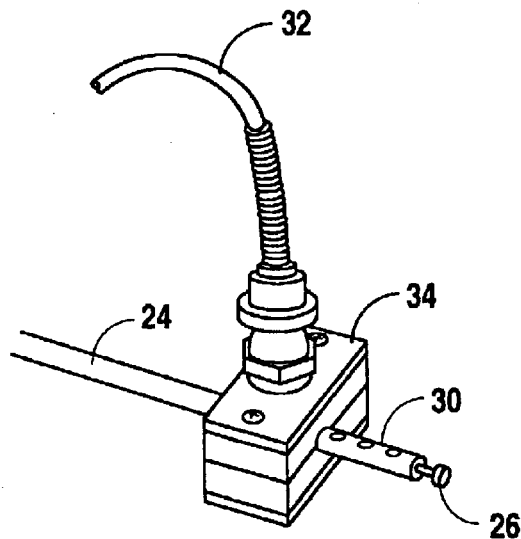
FIG. 5 is a perspective view of the transducer attached to the cable ribbon.

Once a sufficient amount of the ribbon cable 24 is exposed, the transducer 34 is attached to the exposed part of the ribbon cable 24 to perform the inspection. The transducer 34 attached to the ribbon cable 24 is shown in FIG. 5. A shear wave couplant and a clamp are used to attach transducer 34 to ribbon cable 24. Shear wave couplant is a viscous liquid introduced between the transducer 34 and the ribbon 24 before transducer 34 is attached to cable 32. Shear wave couplant allows the ultrasound from transducer 34 to be induced into the ribbon cable 24.

After the transducer 34 is attached to the ribbon cable 24, all of the electronic parts are adjusted to generate a tone burst of 200 kHz. When the transducer 34 generates guided waves into a straight ribbon cable 24 with no defects, a reflection from the end of ribbon cable 24 is observed. A reverberation of initial tone burst exists at the beginning of the waveform which can prevent detection of defects at the beginning of the ribbon cable 24 which is typically within 14 feet from the engine side. However, most cable failures have occurred near the cockpit end of cable 25 which exists at 18 to 29 feet from the engine side.

In order to test the effectiveness of the present method, defects in the throttle cable 25 were simulated by making saw-cut notches in ribbon cable 24. The notches were made in several stages to determine the minimum size notch detected. All initial notches were made with a 0.018 inch thick diamond saw, and they originated from the side of the ribbon cable 24 and grew inward. Notches were intentionally introduced around critical points, particularly bend locations.

FIG. 6 shows the progression in size of the straight notch in test cable #3 when it is laid straight with no bends and no clamp. When saw-cut notches were made in test cable #3, the first notch was made at approximately 27 feet from the engine end of throttle cable 25 as shown at line 62. The distance as measured from the engine end is indicated in feet on the y-axis. The notch depth was increased in several stages from 5 to 50 percent of ribbon cable 24 cross section as shown on the x-axis 64 to determine the minimum detectable defect size. As shown, the notch can be detected when its size exceeds 20 percent of the ribbon cable's 24 cross-section as shown beginning at 66.

Figure 7:
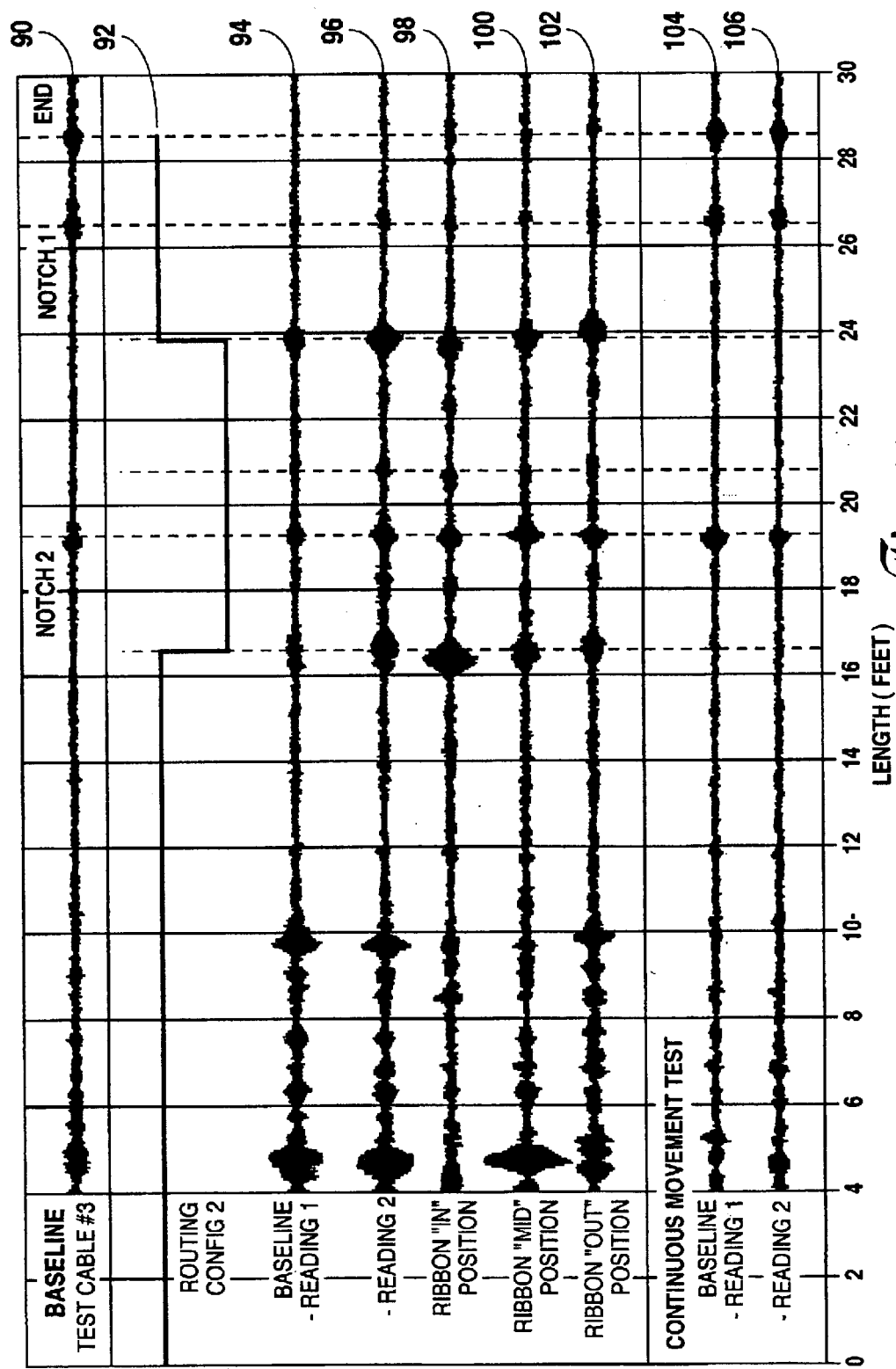
FIG. 7 is a graph of the waveforms from test cable #3 with cable ribbon being moved (a) to different locations inside the sheath and (b) continuously inside the sheath, both during tests.

Next, experiments were performed to determine the ability of the present procedure to detect defects when the ribbon cable 24 is placed in a sheath in its actual state within the aircraft, that is, when the throttle cable 25 goes through several bends. FIG. 7 is a graph of the waveforms from test cable #3 when the ribbon cable 24 is moved within sheath 14. Test cable #3 is given two notches and it is placed through four bends. The first waveform 90 shows the reflection when cable 25 is laid straight with no bends. Next, the routing of the cable 25 is shown at 92. Two readings of the waveform with the bends were plotted at 94 and 96. The next three waveforms, 98, 100 and 102, show the ribbon cable 24 position in relation to sheath 14. Waveform 98 shows ribbon cable 24 all the way inside sheath 14, waveform 100 shows ribbon cable 24 out of the sheath 14 halfway, and waveform 102 shows ribbon cable 24 out as far as possible. The averaging of waveforms 98, 100, and 102 will reduce the reflections from bends. However, the reflections from notches are unchanged. The averaged waveforms 104 and 106 were obtained while the ribbon cable 24 was continuously moving in and out of sheath casing 14.

The averaging technique of the present invention allows defects, such as notches, to be distinguishable from the discontinuities, such as reflections from ball bearings at bends.

Figure 8:
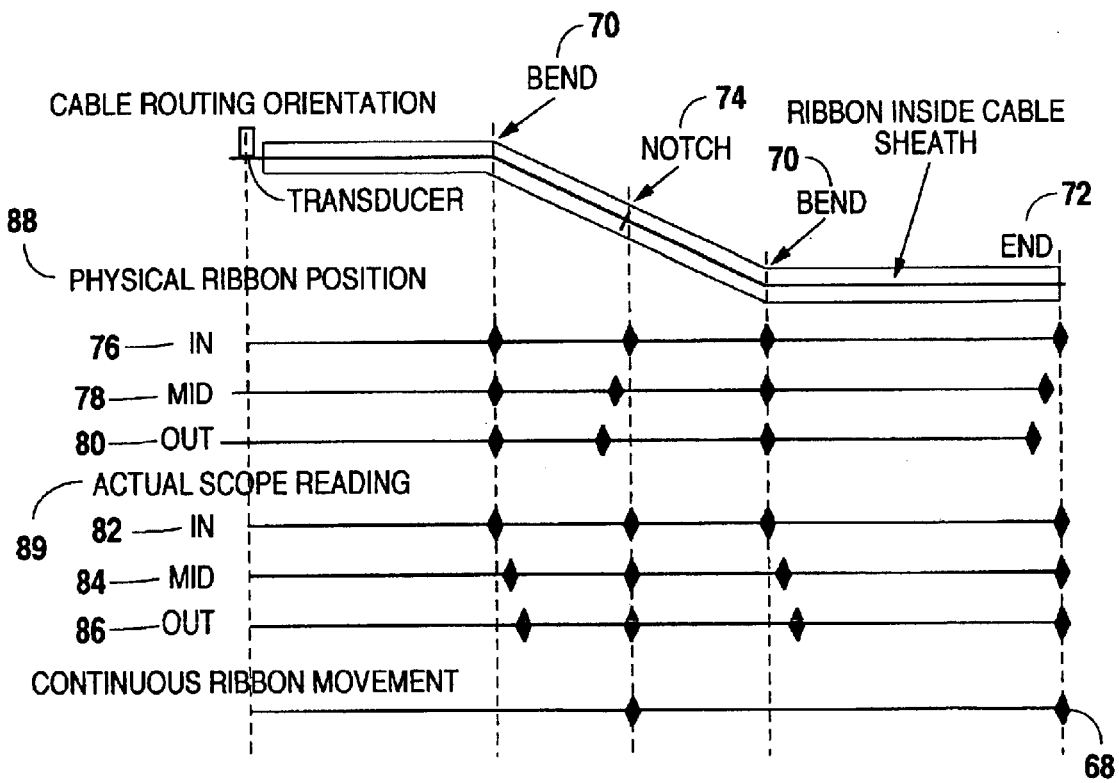
FIG. 8 is a schematic view of the averaged waveforms when cable ribbon is moved inside the sheath.

FIG. 8 is a schematic view of signals from the reflections from notches and bends when the ribbon cable 24 is moved within the sheath casing 14 for two cases. In the first case, 88, the position of the transducer is fixed with respect to the sheath casing 14, and the ribbon cable 24 slides under it. In the second case, 89, the transducer is attached to the ribbon 24, and its position relative to the sheath casing 14 is changed. The throttle cable 25 goes through two bends 70. End 72 can be seen in the reflected signals. A notch 74 is placed between bends 70. For the physical ribbon position 88 of FIG. 8, the ribbon cable 24 within the throttle cable 25 is moved, but the transducer 34 remains fixed with respect to the sheath casing 14. If the ribbon cable 24 is pushed all the way in as indicated at 76, then a signal will be returned for both bends 70, the notch 74 and the end 72. If the ribbon cable 24 is moved midway out as indicated at 78, the bends 70 will be located at the same place; however, the notch 74 and the end 72 have moved closer to the transducer 34. When the ribbon cable 24 is moved as far out as possible as indicated in 80, again the bends 70 will be located at the same place, but the notch 74 and end 72 will be moved still closer to the transducer 34.

For the case when the transducer is fixed to the ribbon cable 24 shown in FIG. 8, the transducer 34 and ribbon cable 24 are moved in unison. When the ribbon cable 24 is pushed all the way in as indicated at 82, the signals for the bends 70, notch 74, and end 72 exist as in 76. However, when the ribbon cable 24 and transducer 34 are moved midway out, the bends 70 will appear farther from the transducer 34 as shown in signal 84. However, notch 74 and end 72 will appear as though they have not moved, since the relative position between the transducer and the notch 74 and end 72 are fixed. In signal 86, the transducer 34 and ribbon cable 24 are pulled out as far as possible. Again notch 74 and end 72 will appear as though they have not moved for the same reasons as noted for signal 84.

In the actual scope readings 89 where the transducer is attached to the ribbon cable 24, the movement of the ribbon cable 24 inside the sheath casing 14 and averaging the waveform over a period of time, will cause the reflections from bends to be greatly reduced. The last waveform 68 shows the average of the waveforms when the ribbon cable 24 is continuously moved in and out indicating both the notch 74 and the end 72, but not the bends 70. The characteristics inside the ribbon cable 24, such as the notch 74 and end 72, remain stationary to the transducer 34 and therefore when they are averaged, they will not change. In experimental conditions, the ribbon cable 24 was placed in several different positions by an actuator (not shown) and the signals for these various positions were averaged. Computer 48 (see FIG. 1) is programmed to deliver a number of signals and receive those signals. Ultimately the averaging is done by computer 48. The entire test can be performed by one person.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A method for inspecting a flexible cable for a defect, said flexible cable having an outer shell and an inner core, said inner core being supported by support structure and longitudinally movable within said outer shell, said method for inspecting comprising:

connecting an ultrasonic transducer to one end of said inner core;

moving said inner core back and forth within said outer shell;

simultaneously transmitting a plurality of tone burst of ultrasonic signals from said transducer along said inner core;

receiving a plurality of reflected ultrasonic signals from said plurality of tone burst of ultrasonic signals;

averaging said plurality of reflected ultrasonic signals to eliminate reflected ultrasonic signals caused by said support structure and leaving reflected ultrasonic signals caused by said defect, if any.

2. The method for inspecting the flexible cable for a defect, said flexible cable having an outer shell and an inner core, said inner core being supported by support structure and longitudinally movable within said outer shell, said method for inspecting of claim 1 further comprising the step of amplifying said tone burst of ultrasonic signals.

3. The method for inspecting the flexible cable for a defect, said flexible cable having an outer shell and an inner core, said inner core being supported by support structure and longitudinally movable within said outer shell, said method for inspecting of claim 1 further comprising the step of modifying said tone burst of ultrasonic signals.

4. The method for inspecting the flexible cable for a defect, said flexible cable having an outer shell and an inner core, said inner core being supported by support structure and longitudinally movable within said outer shell, said method for inspecting of claim 1 further comprising the step of separating the transmitted tone burst of ultrasonic signals of said transmitting step from the reflected signals of said receiving step.

5. The method for inspecting the flexible cable for a defect, said flexible cable having an outer shell and an inner core, said inner core being supported by support structure and longitudinally movable within said outer shell, said method for inspecting of claim 1 further comprising the step of displaying said reflected ultrasonic signals on a computer.

6. The method for inspecting the flexible cable for a defect, said flexible cable having an outer shell and an inner core, said inner core being supported by support structure and longitudinally movable within said outer shell, said method for inspecting of claim 1 wherein said tone burst of ultrasonic signals is a gaussian shaped signal.

7. The method for inspecting the flexible cable for a defect, said flexible cable having an outer shell and an inner core, said inner core being supported by support structure and longitudinally movable within said outer shell, said method for inspecting of claim 1 wherein said ultrasonic transducer has a band width of about 200 KHz to about 800 KHz.

8. The method for inspecting the flexible cable for a defect, said flexible cable having an outer shell and an inner core, said inner core being supported by support structure and longitudinally movable within said outer shell, said method for inspecting of claim 1 further comprising the step of accessing one end of said inner core.

9. The method for inspecting the flexible cable for a defect, said flexible cable having an outer shell and an inner core, said inner core being supported by support structure and longitudinally movable within said outer shell, said method for inspecting of claim 1 wherein said tone burst of ultrasonic signals is generated by a function generator computer card.

10. The method for inspecting the flexible cable for a defect, said flexible cable having an outer shell and an inner core, said inner core being supported by support structure and longitudinally movable within said outer shell, said method for inspecting of claim 1 wherein said tone burst signals are ultrasonic signals.

11. An averaged guided wave inspection method for a throttle cable comprising the steps of:

(a) accessing an end of said throttle cable;

(b) applying a transducer to a ribbon located within said throttle cable;

(c) first moving said ribbon to position one of a plurality of positions to begin scanning;

(d) transmitting an ultrasonic signal in said ribbon;

(e) propagating an elastic wave down said ribbon;

(f) reflecting said elastic wave from any discontinuity in cross section of said ribbon;

(g) receiving said reflected elastic wave with a receiver;

(h) recording the waveform of said transmitting step and said receiving step;

(i) repeating steps (c) through (h) as said ribbon is moved to each of said plurality of positions;

(j) averaging results from said waveforms to eliminate random or support noise leaving only signals caused by changes in cross sectional area of said ribbon, said signals indicating defects, if any exist.

12. The averaged guided wave inspection method for a throttle cable of claim 11 further comprising the step of generating an ultrasonic tone burst before said transmitting step.

13. The averaged guided wave inspection method for a throttle cable of claim 11 further comprising the step of first passing said received signal into an amplifier to amplify the received signal after said receiving step.

14. The averaged guided wave inspection method for a throttle cable of claim 11 wherein said elastic wave of said propagating step is low frequency.

15. The averaged guided wave inspection method for a throttle cable of claim 11 wherein said ultrasonic signal is an ultrasonic guided wave.

16. The averaged guided wave inspection method for a throttle cable of claim 11 wherein said transducer has a band width of about 200 kHz to about 800 kHz.

17. The averaged guided wave inspection method for a throttle cable of claim 11 further comprising the step of replacing a long sleeve telescopic spacer with a short sleeve telescopic spacer to gain access to said end of said throttle cable.

18. The averaged guided wave inspection method for a throttle cable of claim 12 further comprising the step of modifying said tone burst by application of a sine wave after said generating step.

19. The averaged guided wave inspection method for a throttle cable of claim 12 wherein said tone burst is generated by a function generator card.

20. The averaged guided wave inspection method for a throttle cable of claim 12 wherein said tone burst is a gaussian signal.

21. The average guided wave inspection method for a throttle cable of claim 12 wherein said ultrasonic tone burst is amplified prior to said transmitting step.

* * * * *